(12) United States Patent
Yates et al.

(10) Patent No.: US 7,780,663 B2
(45) Date of Patent: Aug. 24, 2010

(54) END EFFECTOR COATINGS FOR ELECTROSURGICAL INSTRUMENTS

(75) Inventors: David C. Yates, West Chester, OH (US);
Phillip Q. Shuster, Maineville, OH (US); Kenneth V. Moran, Loveland, OH (US); Chester O. Baxter, III, Loveland, OH (US); David A. Witt, Maineville, OH (US); James R. Giordano, Milford, OH (US); Jesse J. Kuhns, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 469 days.

(21) Appl. No.: 11/534,326

(22) Filed: Sep. 22, 2006

(65) Prior Publication Data

US 2008/0077131 A1 Mar. 27, 2008

(51) Int. Cl.
*A61B 18/18* (2006.01)
*A61B 17/08* (2006.01)

(52) U.S. Cl. ......................................... 606/51; 606/151

(58) Field of Classification Search .................. 606/41, 606/45–52, 151–153; 227/175.1, 176.1, 227/181.1
See application file for complete search history.

(56) References Cited

U.S. PATENT DOCUMENTS

| 5,201,900 A | * | 4/1993 | Nardella | 606/157 |
| 5,382,247 A | * | 1/1995 | Cimino et al. | 606/33 |
| 5,389,098 A | * | 2/1995 | Tsuruta et al. | 606/41 |
| 5,395,363 A | * | 3/1995 | Billings et al. | 606/41 |
| 5,396,900 A | * | 3/1995 | Slater et al. | 600/564 |

(Continued)

FOREIGN PATENT DOCUMENTS

EP 1 407 719 4/2004

(Continued)

OTHER PUBLICATIONS

European Search Report dated Feb. 19, 2008 for Application No. EP 07253745.

(Continued)

*Primary Examiner*—Michael Peffley
(74) *Attorney, Agent, or Firm*—Frost Brown Todd LLC (57) ABSTRACT

An electrosurgical stapling instrument includes an end effector capable of applying bipolar RF energy into tissue. The end effector has a first pole electrode and a second pole electrode for forming an RF contact circuit with tissue. At least one of the electrodes may have a dielectric coating thereon to create a RF circuit with tissue. The dielectric coating can cover one of the electrodes to create a capacitive coupling circuit with tissue, or can have at least one open passageway extending through the dielectric coating to enable tissue contact with the electrode and the passage of RF energy therethrough. The dielectric coating on the electrode can be masked to create passageways through the dielectric, or the dielectric coating can be locally removed with a variety of techniques to form passageways. The dielectric coating may provide a barrier to prevent shorting between the dielectrically coated electrode and a conductive fastener embedded within tissue. Alternately, a cartridge coating can be used to reduce an electric surface sheet charge on the cartridge thermoplastic that can occur during the application of RF energy to tissue.

25 Claims, 12 Drawing Sheets

U.S. PATENT DOCUMENTS

| | | | |
|---|---|---|---|
| 5,673,841 A | 10/1997 | Schulze et al. | |
| 5,674,220 A * | 10/1997 | Fox et al. | 606/51 |
| 5,688,270 A | 11/1997 | Yates | |
| 5,709,680 A * | 1/1998 | Yates et al. | 606/50 |
| 5,735,848 A | 4/1998 | Yates et al. | |
| H001745 H * | 8/1998 | Paraschac | 606/51 |
| 5,810,811 A * | 9/1998 | Yates et al. | 606/50 |
| 5,833,690 A | 11/1998 | Yates et al. | |
| 6,003,517 A * | 12/1999 | Sheffield et al. | 128/898 |
| 6,139,547 A | 10/2000 | Lontine et al. | |
| 6,533,781 B2 * | 3/2003 | Heim et al. | 606/45 |
| 6,602,252 B2 | 8/2003 | Mollenauer | |
| 6,626,901 B1 * | 9/2003 | Treat et al. | 606/29 |
| 6,840,937 B2 | 1/2005 | Van Wyk | |
| 7,182,763 B2 * | 2/2007 | Nardella | 606/41 |
| 7,207,471 B2 * | 4/2007 | Heinrich et al. | 227/181.1 |
| 2002/0062136 A1 * | 5/2002 | Hillstead et al. | 606/205 |
| 2002/0165541 A1 * | 11/2002 | Whitman | 606/48 |
| 2004/0068307 A1 | 4/2004 | Goble | |
| 2004/0181219 A1 | 9/2004 | Goble et al. | |
| 2005/0021025 A1 * | 1/2005 | Buysse et al. | 606/51 |
| 2005/0197659 A1 * | 9/2005 | Bahney | 606/51 |
| 2006/0052778 A1 | 3/2006 | Chapman et al. | |

FOREIGN PATENT DOCUMENTS

| | | |
|---|---|---|
| EP | 1 520 523 | 4/2005 |
| GB | 1 399 216 | 6/1975 |

OTHER PUBLICATIONS

Examination Report dated Mar. 4, 2008 for Application No. EP 07253745.

Examination Report dated Oct. 8, 2009 for Application No. EP 07254735.

* cited by examiner

END EFFECTOR COATINGS FOR ELECTROSURGICAL INSTRUMENTS

FIELD OF THE INVENTION

The present invention relates, in general, to an electrosurgical instrument and, more particularly, to coatings for an electrosurgical instrument which uses thermogenic energy for cauterization, coagulation and tissue joining/welding in combination with staples to form a hemostatic staple/coagulation/cut line in tissue.

BACKGROUND OF THE INVENTION

Surgical procedures frequently require cutting of tissue which can cause bleeding at the operative or surgical site. Hemostasis, or the arrest of bleeding, is important to surgeons to reduce blood loss and reduce surgical complications. A variety of hemostatic control techniques are available to the surgeon such as suturing, stapling, the application of surgical clips, the application of ultrasonic energy, the application of laser energy, as well as the application of monopolar or bipolar electrical energy. Surgeons frequently use a combination of these means to induce hemostasis during surgery. For open procedures, the surgical site is readily accessible through the large incision and the application of devices or techniques to reduce bleeding are readily applied. Endoscopic surgery is done through small access ports inserted into small incisions. Endoscopic surgeries are more challenging as the surgeon does not have the large incision to work through, visibility of the site is more difficult, and access to the surgical site is limited to the number of small access ports or trocars. Electrocautery instruments are commonly used when accessing a patient during surgery. These instruments apply monopolar or bipolar Radio Frequency (RF) energy to cauterize the local "bleeders" in tissue incisions. Monopolar instruments have one electrode that is associated with a cutting or cauterizing instrument and a return or ground electrode is attached to a remote portion of the patient. Energy is applied to the bleeder by delivering energy from a tip of the device to the patient at the site of the bleeder.

Bipolar instruments normally apply a cauterizing current to a pair of electrodes on moveable opposed jaw members of the instrument. Tissue is cauterized by clamping the open jaw members upon tissue to bring the electrodes into tissue contact, and then applying RF bipolar energy to the compressed tissue within the jaw members. The current conducts between the electrodes and cauterizes, coagulates, or tissue welds the tissue compressed therebetween.

Additionally, mechanical devices such as surgical staplers and linear cutters, both open and endoscopic, have been utilized as a means of excising tissue and controlling hemostasis. Staples are used to provide hemostasis in vascular structures, and when applied to lung tissue, were found to provide a good degree of pneumostasis as well. Surgical cutters have a plurality of staples held in multiple staggered rows in a replaceable cartridge. The cutters compress the tissue, and the staples are formed or fired into the compressed tissue in close proximity to the diseased tissue portion that is to be excised. A cutting blade passes longitudinally between the innermost rows of formed staples, transecting the tissue. The cutter is removed from the surgical site, reloaded with another unfired stapling cartridge, and the procedure is repeated until the desired section of the lung is resected and removed.

One known problem which can arise with using surgical staplers in this fashion has been the formation of small "bleeders" in the cut and stapled tissue. To ensure peace of mind, surgeons can suture or use other techniques to staunch the small bleeders. RF energy devices and/or ultrasonic energy devices are frequently used to cut and coagulate tissue during endoscopic surgery. However, energy delivery to tissue next to a metallic staple line can require care and technique. With bipolar RF devices, a staple can cause a short and prevent the RF generator from firing and coagulating tissue. With ultrasonic and/or monopolar devices, contact with staples can conduct energy away from the initial application site.

U.S. Pat. No. 5,735,848, U.S. Pat. No. 5,688,270, and U.S. Pat. No. 5,709,680 by Yates et al. disclose surgical instruments that combine a staple applying endocutter with an electrosurgical bipolar RF device to improve hemostasis, reduce surgical complexity, and operating room time. With these improved bipolar cutting and stapling devices, activation of the clamping trigger puts tissue in contact with a first and second electrode, and activation of the electrosurgical generator, typically with a foot pedal, produces a narrow stripe of coagulated tissue with the application of RF energy. The first electrode, the clamped tissue, and the second electrode form a conductive circuit. The moisture and ions within the tissue chemistry conducts the RF energy, and the tissue begins to desiccate or coagulate. As the tissue desiccates, it becomes less and less conductive. When the tissue is fully desiccated, it is nearly an insulator and only a small amount of current flows between the first and second electrodes. Activation of a second firing trigger on the surgical instrument fires rows of staples from a single shot staple cartridge on either side of the coagulation stripe, and places a cut line along the center of the coagulated tissue. When the surgical instrument is opened, the tissue cut line is cauterized along the edge for hemostasis, and has multiple parallel rows of staple lines placed in the un-cauterized tissue flanking the cauterized cut edge for additional security.

If a longer cut line is needed, the surgeon reloads a second staple cartridge into the electrosurgical stapling instrument, and reinserts it into the patient at the desired location. The instrument is then re-clamped, and the generator is again activated to produce a second coagulation stripe. In some cases, it is desirable to place the second coagulation stripe and staple line over the first staple line. This can occur when the second cut line is at an angle to the first. Placing and clamping the end effector over the first staple line can create a "short" condition by shorting the first and second electrodes of the electrosurgical stapler through one or more staples. The metal staples are far more conductive to RF energy than tissue in any condition. When the electrodes are shorted, the RF current preferentially flows through the staple and not through the tissue. For a short, the surgeon must unclamp the instrument and reposition and reclamp the end effector at another location. If the instrument shorts again, the instrument must again be repositioned until shorting is eliminated. What is needed is an improved electrosurgical stapling device that decreases operating room time by reducing the ability to cause shorts.

Additionally, in electrosurgical devices that combine staples with RF energy delivery, the application of RF energy can create a surface charge with the plastic cartridge. Cartridge materials are commonly plastics chosen for strength, moldability, thin walls, and dimensional accuracy or repeatability. What is needed is a cost effective way to reduce the surface charge of the cartridge.

Alternately, it may be desirable to use capacitive coupling of RF energy to coagulate the tissue. Classical bipolar RF electrosurgical devices form a conductive resistance network to coagulate tissue. Conductive coupling devices also use RF bipolar energy, but transfer energy from one circuit to another by means of the mutual capacitance between the circuits. A capacitive coupling RF bipolar electrosurgical device places a non-conductive material or dielectric between the tissue and at least one of the electrodes. The transfer of energy from the shielded electrode to the unshielded electrode is by means of the mutual capacitance between the first pole electrode dielectric, tissue and second pole electrode circuit.

At present, there are no known electrosurgical instruments that can meet all of the needs outlined above. These and other advantages will become more apparent from the following detailed description and drawings.

SUMMARY OF THE INVENTION

In accordance with the present invention, there is provided an electrosurgical instrument having an end effector capable of receiving RF bipolar energy therein. The end effector has a first pole electrode and a second pole electrode. A dielectric coating can be placed on at least one of the first and second pole electrodes, the dielectric having least one open channel through the dielectric coating. The at least one open channel in the dielectric coating may provide passage of radio frequency energy between the first and second pole electrodes.

Also in accordance with the present invention, there is provided an electrosurgical instrument having an end effector capable for clamping and coagulating tissue. The end effector can have a first pole electrode and a second pole electrode. A dielectric coating may be placed on at least one of the first and second pole electrodes where the dielectric coating can prevent direct tissue contact with at least one of the electrically active electrodes.

Yet another embodiment in accordance with the present invention is an electrosurgical instrument having an end effector capable of receiving bipolar energy and placing at least one staple into tissue. The end effector may have a first pole electrode, a second pole electrode; and a staple cartridge having said at least one staple therein. The staple cartridge can have a coating to reduce formation of a surface charge thereon during the application of bipolar energy to tissue.

BRIEF DESCRIPTION OF THE DRAWINGS

The novel features of the invention are set forth with particularity in the appended claims. The invention itself, however, both as to organization and methods of operation, together with further objects and advantages thereof, may best be understood by reference to the following description, taken in conjunction with the accompanying drawings in which:

DETAILED DESCRIPTION OF THE INVENTION

Figure 1:
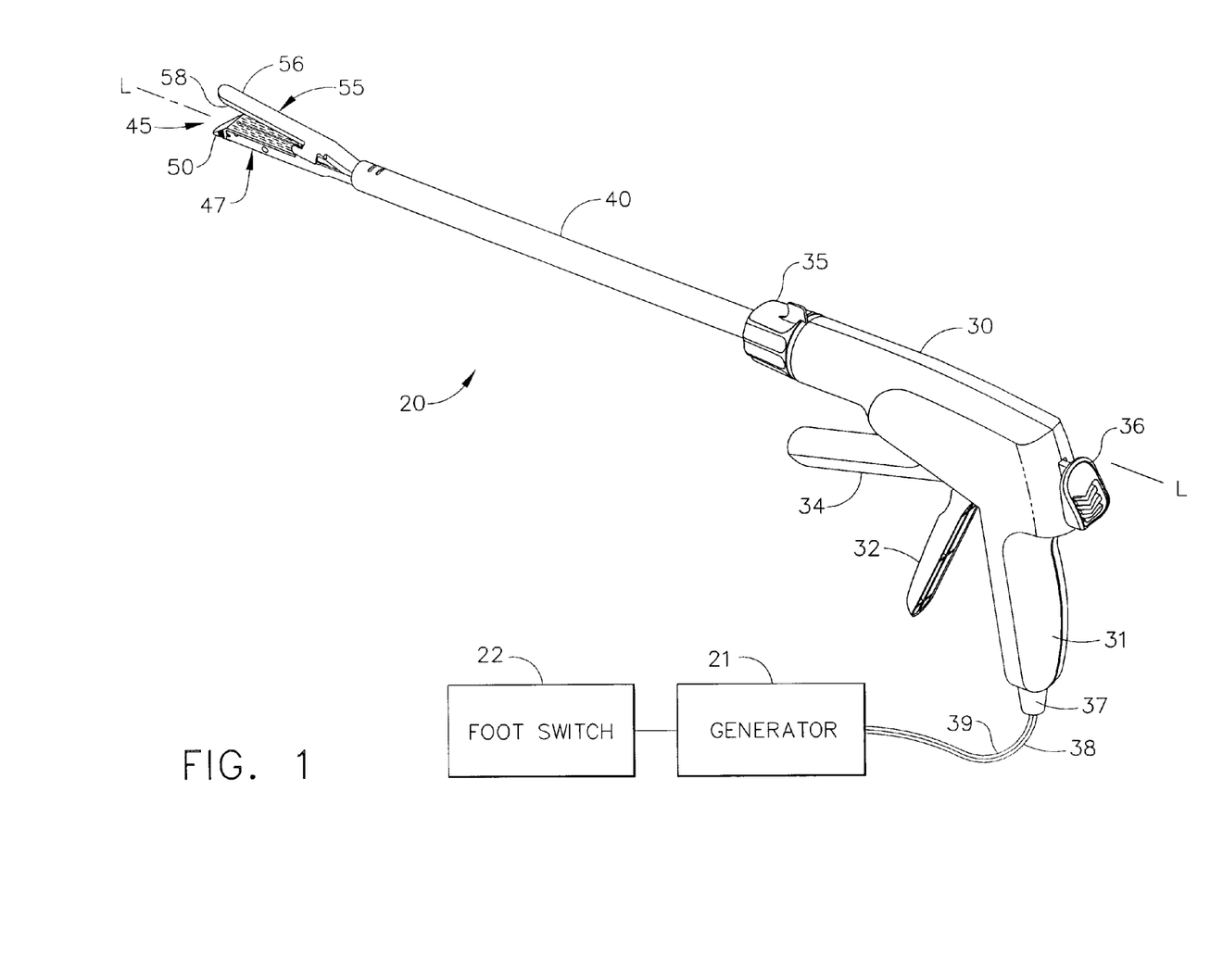
FIG. 1 is an isometric view of an electrosurgical instrument of the present invention, showing an electrosurgical generator operably coupled to an actuation foot switch and to an electrosurgical instrument having a distal end effector with an angularly open anvil.

As best shown in FIG. 1, the present invention includes an electrosurgical instrument, generally designated 20, used for the cauterization, coagulation and/or tissue welding in the performance of surgical procedures. Electrosurgical instrument 20 clamps on tissue, can apply RF energy for tissue coagulation, and can be fired to place a plurality of parallel rows of staples and cut tissue between the innermost rows of staples. Electrosurgical instruments of this type are described in the U.S. Pat. No. 5,735,848, U.S. Pat. No. 5,688,270 and U.S. Pat. No. 5,709,680 by Yates et al. which are incorporated herein by reference. However, the electrosurgical instrument 20 can have coating improvements to an end effector 45 that will be described in detail below.

Figure 3:
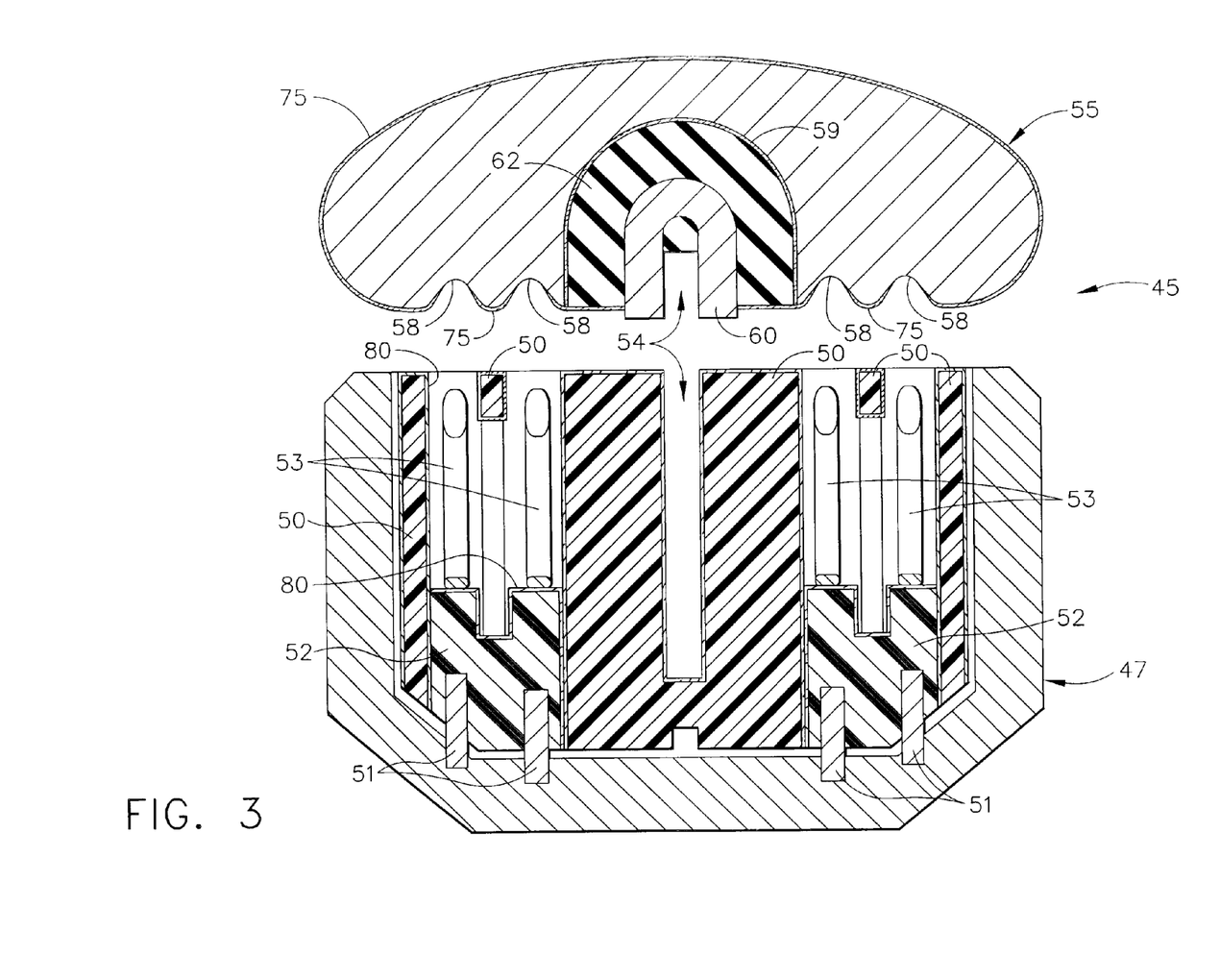
FIG. 3 is a cross sectional end view of the end effector of FIG. 1 with the anvil in a closed position, the cross section taken along lines A-A (FIG. 2) and showing the anvil and cartridge coatings.

The electrosurgical instrument 20 has a handle 30 and a shaft 40 extending distally from the handle 30. End effector 45 extends distally from a distal end of the shaft 40. Rotation knob 35 is located between the handle 30 and shaft 40 for simultaneous rotation of the shaft 40 and the end effector 45 about a longitudinal axis LL. End effector 45 extends distally from shaft 40 and has a moveable anvil 55 and a fixed lower channel 47. Anvil 55 is moveable from a first open position FIG. 1) angled away from the channel 47 to a second clamped or closed position parallel to and spaced away from channel 47 (FIG. 3). A cartridge 50 containing a plurality of staples 53 (FIG. 3) is removably mounted within the channel 47. A closure trigger 32 and a firing trigger 34 are rotatably mounted within the handle 30 near a grip 31. Actuation of closure trigger 32 rotates the trigger adjacent to grip 31, closes of the anvil 55, and unlocks of the firing trigger 34. Actuation of the firing trigger 34 ejects the plurality of staples 53 and moves a knife 66 between the inner most rows of staples 53 (not shown). Release button 36 is located at the proximal end of the handle 30 for opening the anvil 55 from its closed position.

RF energy is supplied to the electrosurgical instrument 20 from an electrosurgical generator 21 when the surgeon activates a foot switch 22. A first pole wire 38 and a second pole wire 39 electrically connect the generator 21 to the electrosurgical instrument 20 for delivery of RF energy to a first and second pole electrode. The first and second pole wires 38 and 39 respectively extend from the generator, into a strain relief 37 and to the first and second pole electrodes in end effector 45.

Figure 2:
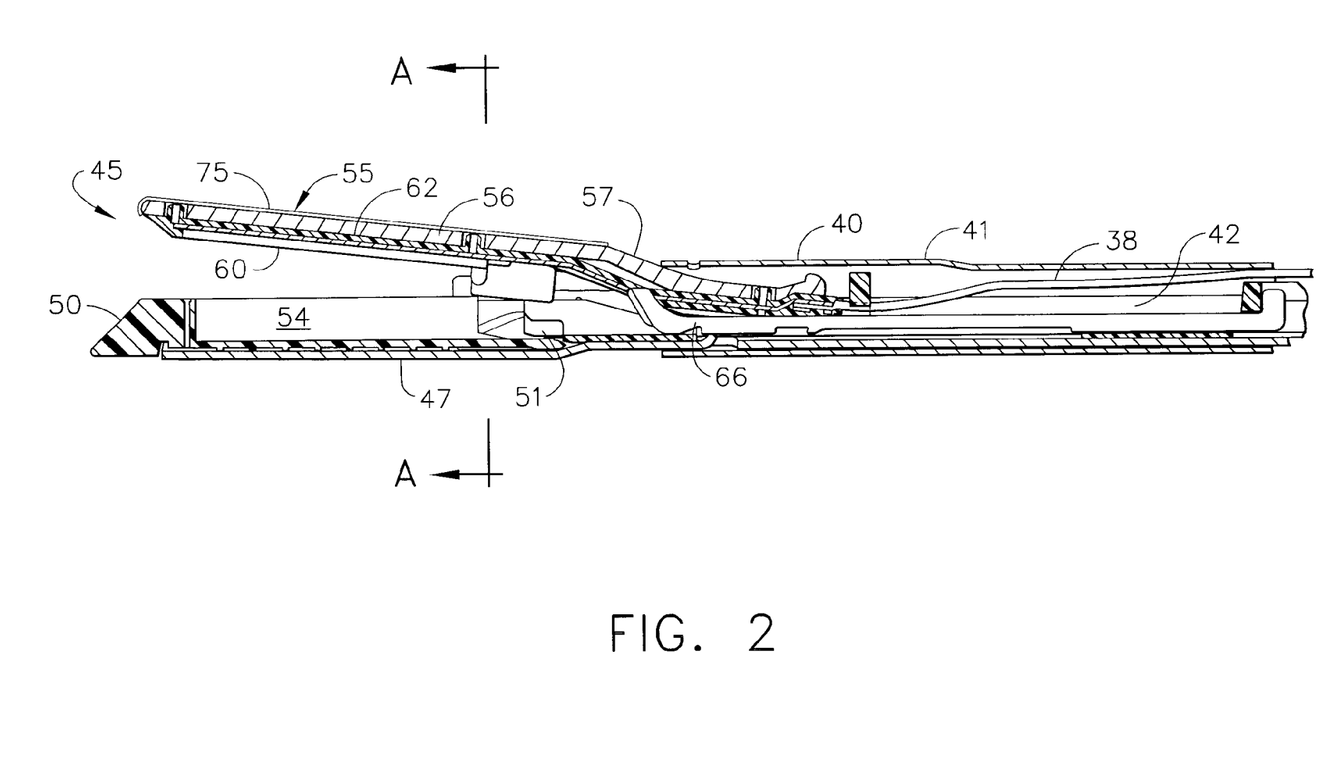
FIG. 2 is a side view, in cross section, of the end effector of the electrosurgical instrument of FIG. 1 showing a first unfired staple cartridge located below the angularly open anvil, and a coating on the anvil.

As best shown in FIG. 2, shaft 40 has a longitudinally moveable hollow closure tube 4 and a longitudinally fixed to a nonconductive retainer 42 made from a suitable material such as glass reinforced polycarbonate. Retainer 42 is rotatably restrained within handle 30 and is prevented from moving longitudinally but allowed to rotate about the longitudinal axis LL Channel 47 is fixed to a distal end of retainer 42, extends distally from closure tube 41, and has anvil 55 moveably mounted within. Anvil 55 can be formed from a conductive material such as stainless steel, and is shown in the open position angularly spaced away from channel 47 and cartridge 50. Anvil 55 contains a plurality of staple forming pockets 58 that are brought into alignment above the staples 53 in the cartridge 50 when anvil 55 is closed (see FIG. 3). A "C" shaped insulator 62 is fixedly attached within groove 59 (FIG. 3) of anvil 55, and a first pole electrode 60 having a tissue contact surface and mounted within the inner portion of the "C". Insulator 62 electrically isolates the first pole electrode 60 from the electrically conductive anvil 55. A distal end of first pole wire 38 forms an electrical connection with first pole electrode 60 and a proximal end is electrically connected to generator 21 (FIG. 1). First pole wire 38 is electrically isolated from all elements of electrosurgical instrument 20 therebetween. Staple forming anvil 55 also acts as the return path or second pole electrode 56 for the electrosurgical device 20 of the present invention. Anvil 55 is closed by activating the closure trigger 32. Closure trigger 32 is operably coupled to closure tube 41 of shaft 40 and moves closure tube 41 distally from a proximal position shown in FIG. 2. This motion brings closure tube 41 into contact with a ramp 57 of anvil 55 and through wedging action, moves anvil 55 to the closed position of FIG. 3. Closure tube 41 is also in sliding and electrical contact with channel 47. The anvil 55 of the present invention is covered in a dielectric or non-conducting coating 75 in selected areas. As shown in FIG. 2, the ramp 57 of the anvil 55 is not coated to ensure an electrically conducting path with the closure tube 41. Closure tube 41 is brought into electrical contact with the second pole wire 39 when the closure trigger 32 is activated to form a second pole electrical circuit extending from the generator 21 to the second pole anvil 55.

Actuation of the firing trigger 34 ejects the staples 53 from the cartridge 50, forms staples 53 against the anvil 55, and move a knife 66 along a knife slot 54 to sever tissue between the inner most rows of staples 53 (action not shown). Firing trigger 34 moves wedge block 51 and knife 66 distally through the cartridge 50 to form the staples 53 against the anvil 55. Knife 66 attaches to the wedge block 51 and moves longitudinally through knife slot 54 within cartridge 50 and first electrode 60 (see FIG. 3) in response to movement of firing trigger 34. Knife 66 trails the formation of the staples 53 so tissue is stapled first and cut second. FIG. 3 is a cross sectional end view AA of the end effector 45 of the present invention when the anvil 55 is in the closed position spaced away from and generally parallel to cartridge 50 and channel 47. See FIG. 2 for the longitudinal location of cross section AA on end effector 45. In FIG. 3, the cross section of the anvil is taken across staple pockets 58, and electrode groove 59.

The electrosurgical instrument of the present invention includes a non-conducting or dielectric anvil coating 75 on anvil 55. By way of example, the dielectric coating 75 could be but is not limited to a PTFE (polytetrafluroethylene), Paralene™ or Parylene™, titanium dioxide, or an epoxy. Paralene™ or Parylene™ are generic names for a series of polymers based on paraxylene and are available from Advance Coating, 10723 Edison Court, Rancho Cucamonga, Calif. 91730. The Parylenes are formed by the pyrolysis of a di-p-xylene (dimer) in a vacuum environment which is then deposited on a cooler (i.e. room temperature) substrate under continuous vacuum. Paralene exhibits excellent dielectric strength, exceptionally high surface and volume resistivities; and electrical properties that are essentially independent of temperature. It provides a conformal, pinhole-free coating that is unexcelled for corrosion resistance and dielectric protection. If desired, coating 75 can be selectively coated onto desired areas of the anvil, or the anvil can be entirely coated. If desired, selected areas of coating 75 may be removed by laser etching, sandblasting, water jet, grinding and the like. As shown in FIG. 2, the anvil coating 75 has been selectively excluded or removed from the ramp 57 to ensure electrical conductivity of the anvil 55 to the closure tube 41. Closure tube 41 is electrically connected to the second pole wire 39 extending from the strain relief 37 to the generator 21 to complete the second pole ground circuit. Anvil 55 and channel 47 are both electrically connected to the second pole wire 39 by contact with closure tube 41. In FIG. 3, anvil coating 75 generally extends around the anvil 55 but does not extend into the plurality of uncoated staple pockets 58 extending upwardly into anvil 55. Additionally, the coating 75 has variable thickness near the staple pockets 58. Insulator 62 is constrained in groove 59 and holds first pole electrode 60.

Cartridge 50 is constructed from an engineering thermoplastic such as the liquid crystal polymer (LCP) Vectra™. Drivers 52 move vertically in cartridge 50 when pushed upwards by wedge block 51 to form staples 53 in anvil pockets 58. Drivers 52 are also constructed from an engineering thermoplastic such as polycarbonate or a liquid crystal polymer (LCP) such as Vectra™. When exposed to RF energy, some engineering thermoplastics can exhibit a strong sheet surface charge which can expose the plastics to high heat and possibly arcing. It is an object of the present invention to provide cartridge coating 80 on the cartridge 50 and/or drivers 52. Cartridge coating 80 can be a dielectric coating, reduce the surface charge effect on the cartridge 50, and prevent potential damage to the cartridge thermoplastics. Additionally, the cartridge coating 80 can provide some degree of thermal protection and/or add lubricity to the cartridge 50 and drivers 52 and, if desired, selectively excluded by masking or removed by laser etching, sandblasting, water jet, grinding and the like. Cartridge coatings 80 can be PTFE (polytetrafluroethylene), a Parlene™ or Parylene™, titanium dioxide, or an epoxy.

Figure 4:
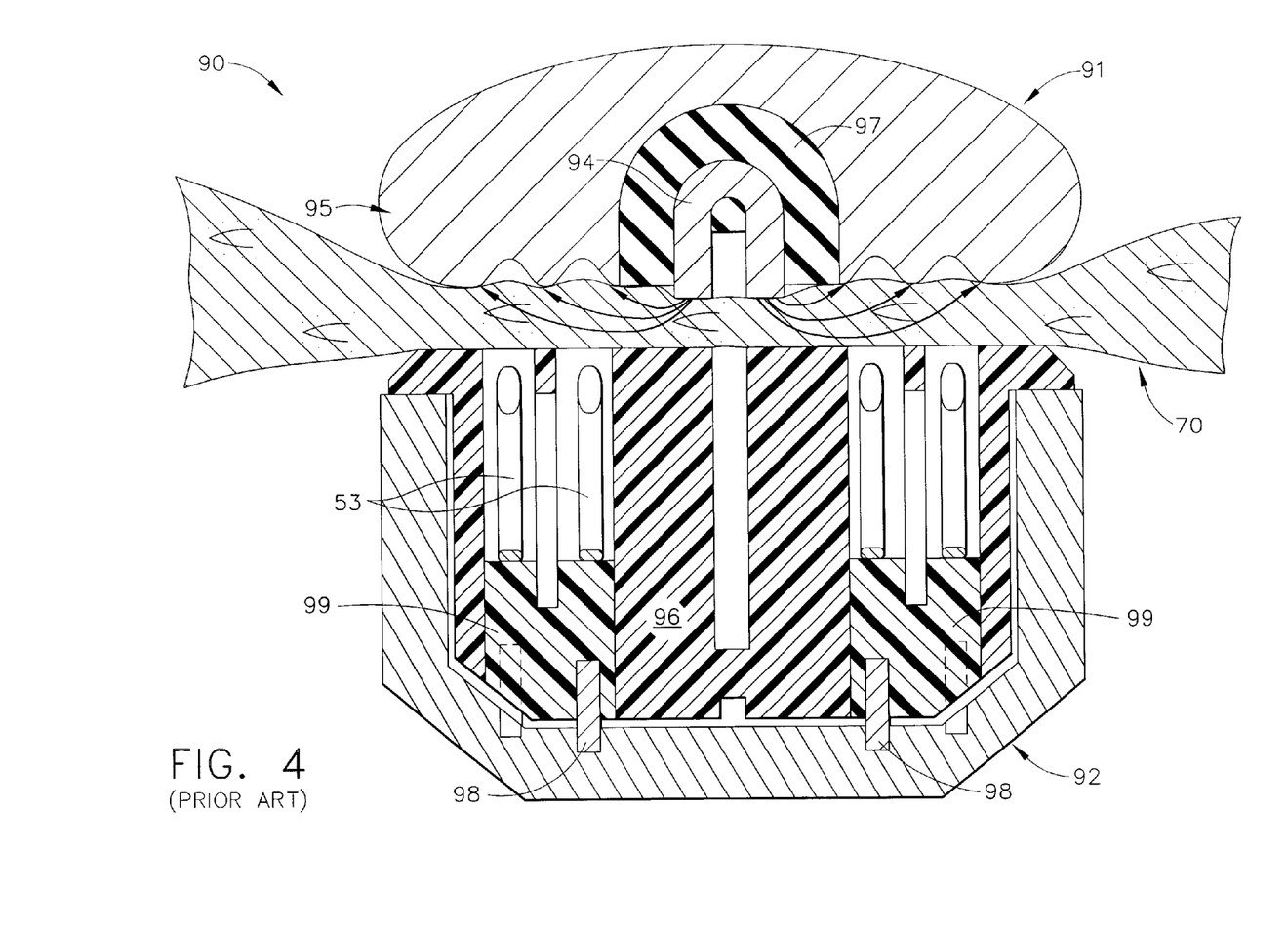
FIG. 4 is a cross sectional end view of a prior art end effector clamped on tissue and showing the path of RF energy between the electrodes.

FIG. 4 is a cross sectional view of a prior art end effector 90 as disclosed in a U.S. Pat. No. 5,833,690 by Yates et al. which is hereby incorporated by reference. In FIG. 4, the prior art end effector 90 is clamped on tissue 70 and current paths from a first pole electrode 94 to a second pole electrode 95 are shown. In this invention, both a prior art anvil 91 and a prior art channel 92 form a prior art second pole electrode 95 (prior art anvil 91) by contact with a prior art closure tube 93 (not shown). Prior art cartridge 96 has staples 53, prior art drivers 97 and prior art wedges 98.

Figure 5:
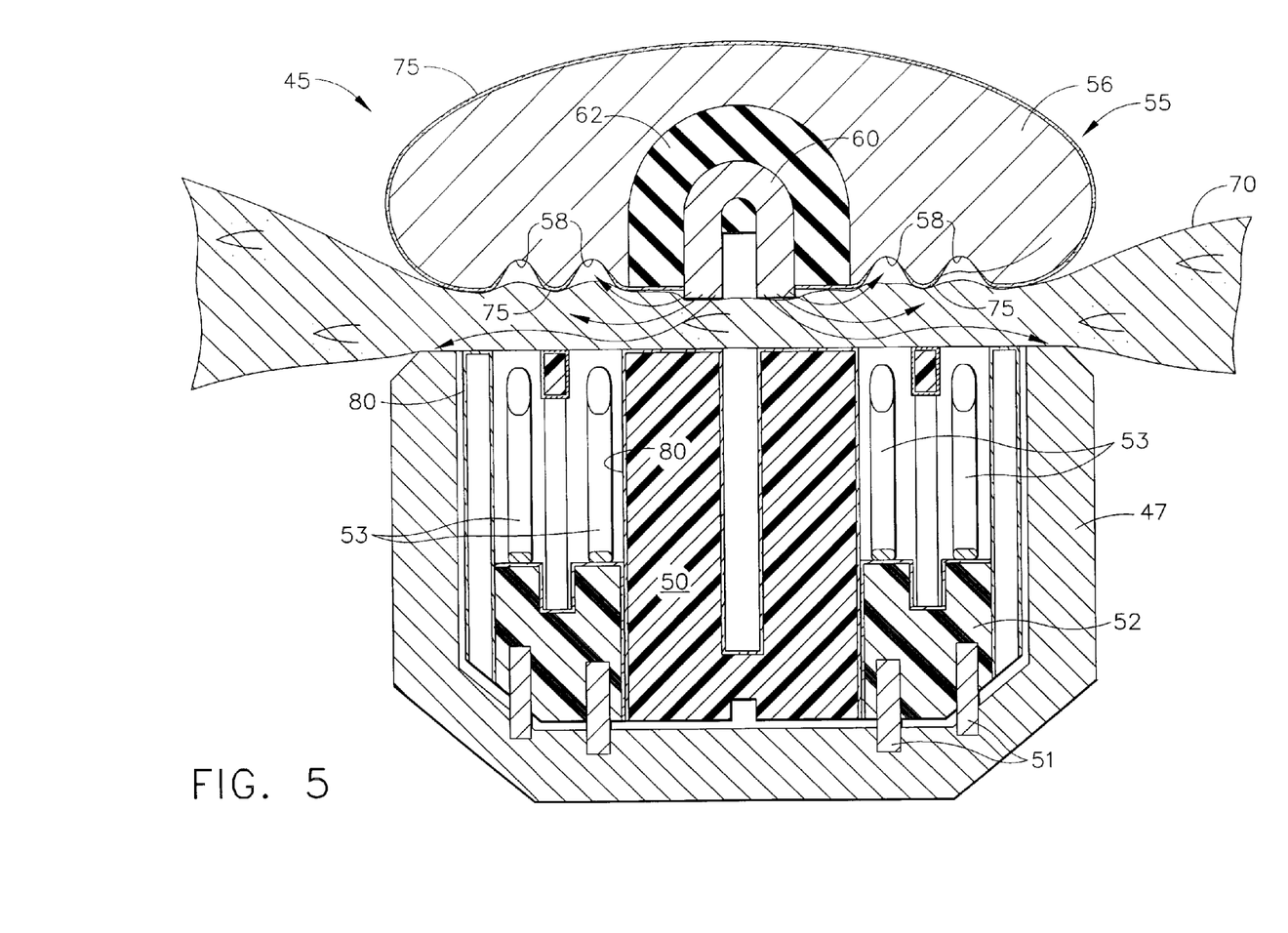
FIG. 5 is a cross sectional view of an end effector with a coated anvil clamped on tissue and showing the RF energy paths into uncoated staple pockets and channel.

FIG. 5 is a cross sectional view of the end effector 45 of the present invention clamped on tissue 70 with RF energy being applied to the tissue. As shown, the anvil coating 75 of the preferred invention redirects current flow to the second pole electrode 56 formed from uncoated staple pockets 58 and uncoated channel 47.

Figure 6:
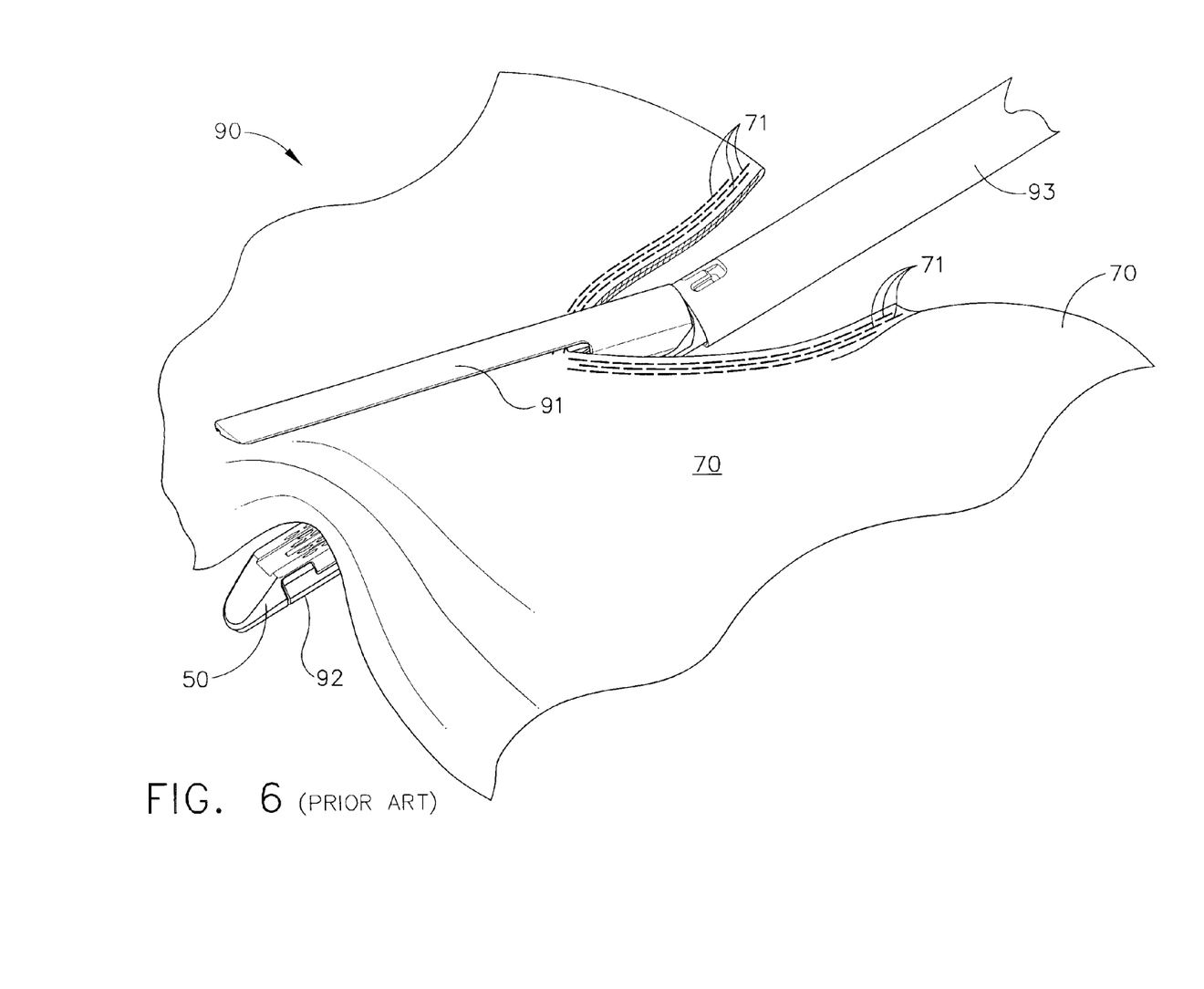
FIG. 6 is an isometric view showing the prior art end effector of FIG. 4 being placed on a portion of severed tissue containing a plurality of formed staples, the prior art end effector of FIG. 4 being positioned for a second clamp, coagulation, staple and cutline on top of the prior staple lines.

FIG. 6 shows the open prior art end effector 90 being placed on top of a previously placed staple line in tissue just prior to placement of a second clamp, coagulation staple and cut line. The first firing of the prior art instrument has formed staples 71 shown extending along the cut line and directly below the first and second electrodes 94 and 95 respectively within anvil 91. A new cartridge 50 containing staples 53 has been loaded for this firing.

Figure 7:
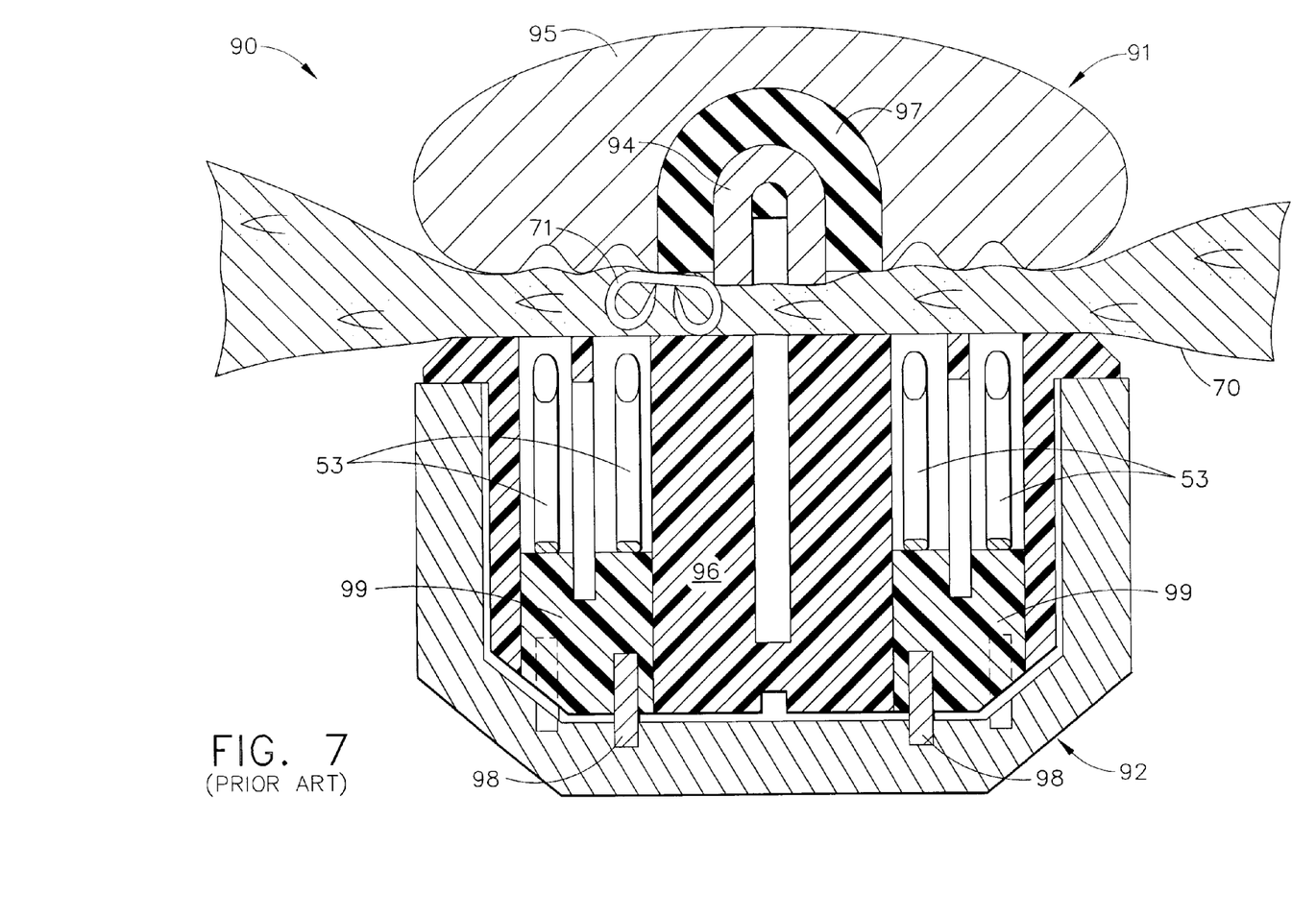
FIG. 7 is a cross sectional view of the prior art end effector of FIG. 6 clamped on the portion of tissue containing a plurality of formed staples and showing how a staple formed in tissue can induce shorting between the first pole electrode and the anvil.

FIG. 7, shows the prior art end effector 90 of FIG. 6 after the prior art anvil 91 is clamped on tissue containing one formed staple 71. The formed staple 71 is in direct contact with the prior art first pole electrode 94, and with the second pole electrode 95 creating an electrical short. The prior art second pole electrode 92 can easily contact the staple 71 and can cause a short condition between the prior art first and second pole electrodes 94, 95 respectively. The short means the surgeon must unclamp the instrument, reposition it, and clamp it again.

Figure 8:
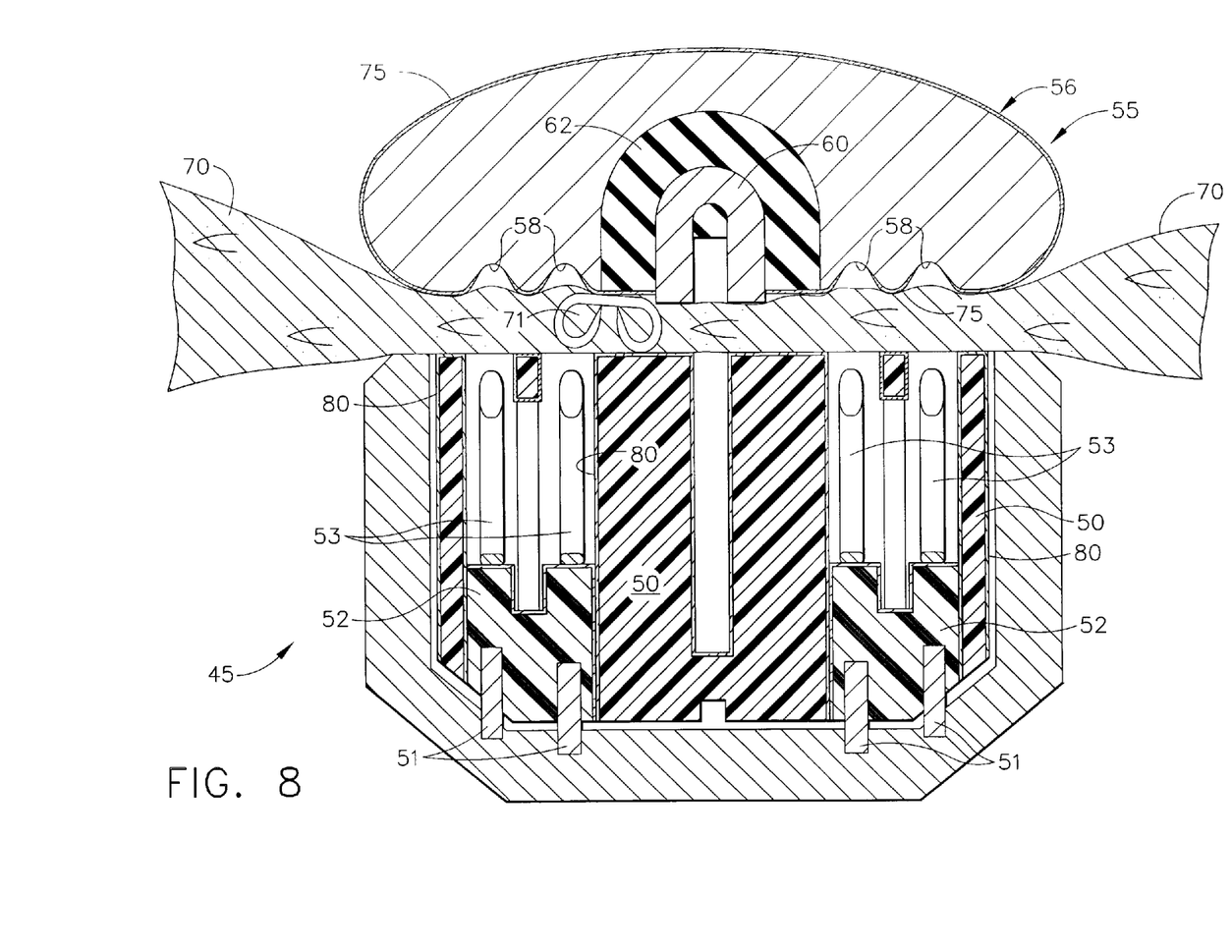
FIG. 8 is a cross sectional view of the end effector of FIG. 5 clamped on the portion of tissue containing a plurality of formed staples and showing how an anvil coating can eliminate shorting with a formed staple.

FIG. 8 is a cross sectional view of the end effector 45 of the present invention clamped on tissue 70 containing one formed staple 71. As shown, the anvil coating 75 prevents the formed staple 71 from contacting the exposed areas of second pole electrode 56 located in staple pockets 58 and "U" shaped channel 47 (extending below cartridge 50—see FIG. 1) and creating an electrical short. Thus, anvil coating 75 of the preferred invention allows current flow through tissue to the staple pockets 58 and channel 47, but prevents the formed staple 71 from easily contacting the second pole electrode 56 and shorting within the end effector 45. Current paths can be to the staple pockets 58 or to the channel 47, or a combination of both. In the presence of staples 71, current paths can also be from first pole electrode 60, to the staple 71, and then to the pockets 58 and channel 47. Electrical energy flows mostly through the path of least resistance though some portion also flows through higher resistance portions of the circuit as well. The current through any individual element of the circuit can be calculated using Ohm's Law (V=IR where V is voltage, I is current and R is the resistance). In the case of the formed staple 71, the least resistive current path (and therefore the path of greatest current flow) is from the first pole electrode 60, through the staple 71, through tissue 70 and into pockets 58. This path coagulates and desiccates tissue 70 adjacent to the formed staple 71. As the tissue 70 near staple 71 desiccates, it becomes more resistive and less current flows to staple pocket 58. With the conductive path through staple 71 and pocket 58 is in contact with more resistive coagulated tissue, the uncoagulated tissue 70 adjacent to the next least resistive path begins to coagulate.

Figure 9:
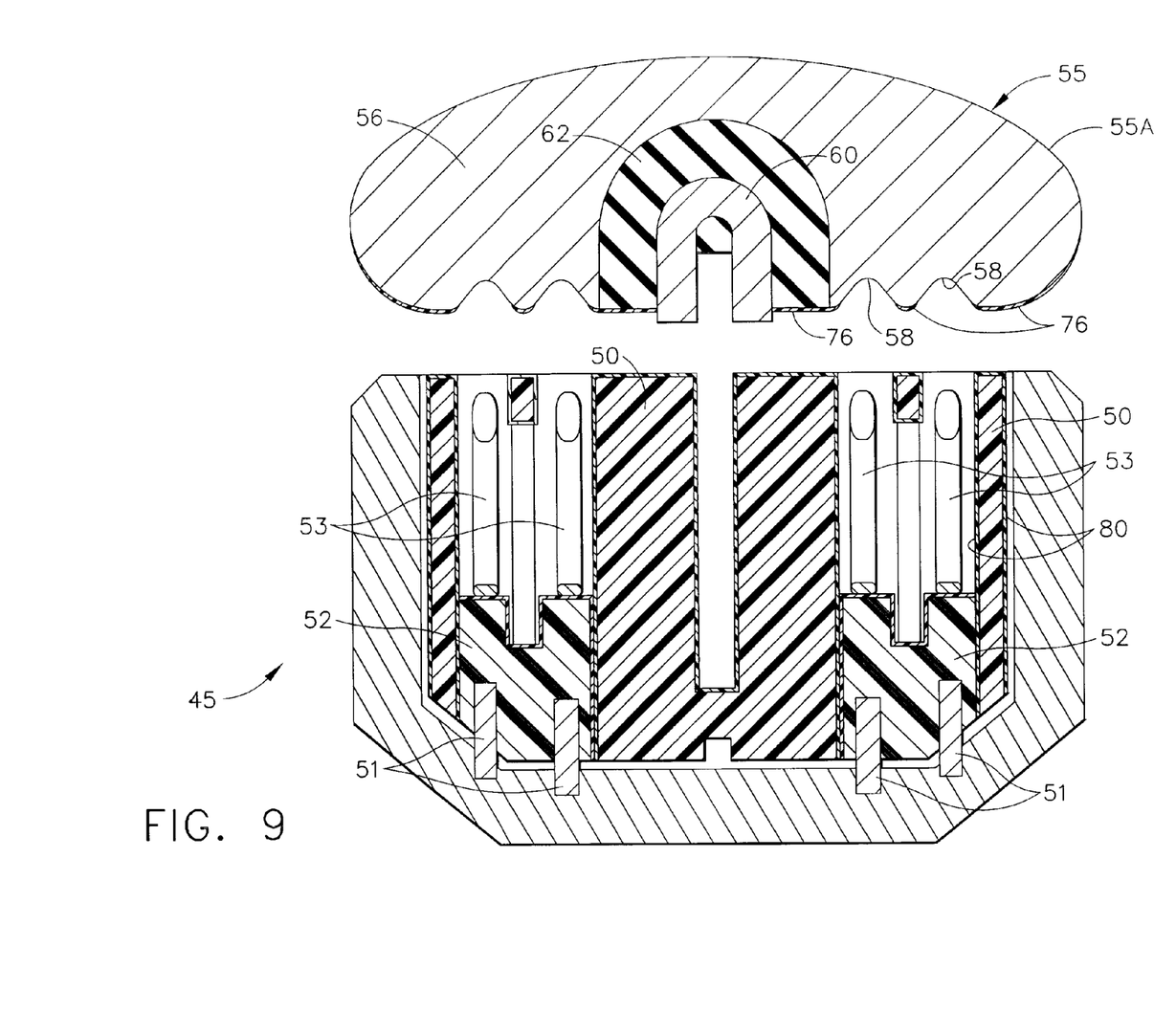
FIG. 9 is an alternate embodiment of the coatings of the present invention with a portion of the coating removed from an upper surface of the anvil.

FIG. 9 is an alternate embodiment of the coatings of the present invention. In this embodiment, alternate anvil coating 76 is masked from or removed from an upper anvil surface 55a, from the staple pockets 58 of the anvil 55, and from the ramp 57 (see FIG. 2) of the anvil 55. This alternate embodiment reduces the area of the alternate anvil coating 76 and the material cost of the coating 76 without reducing effectiveness.

Figure 10:
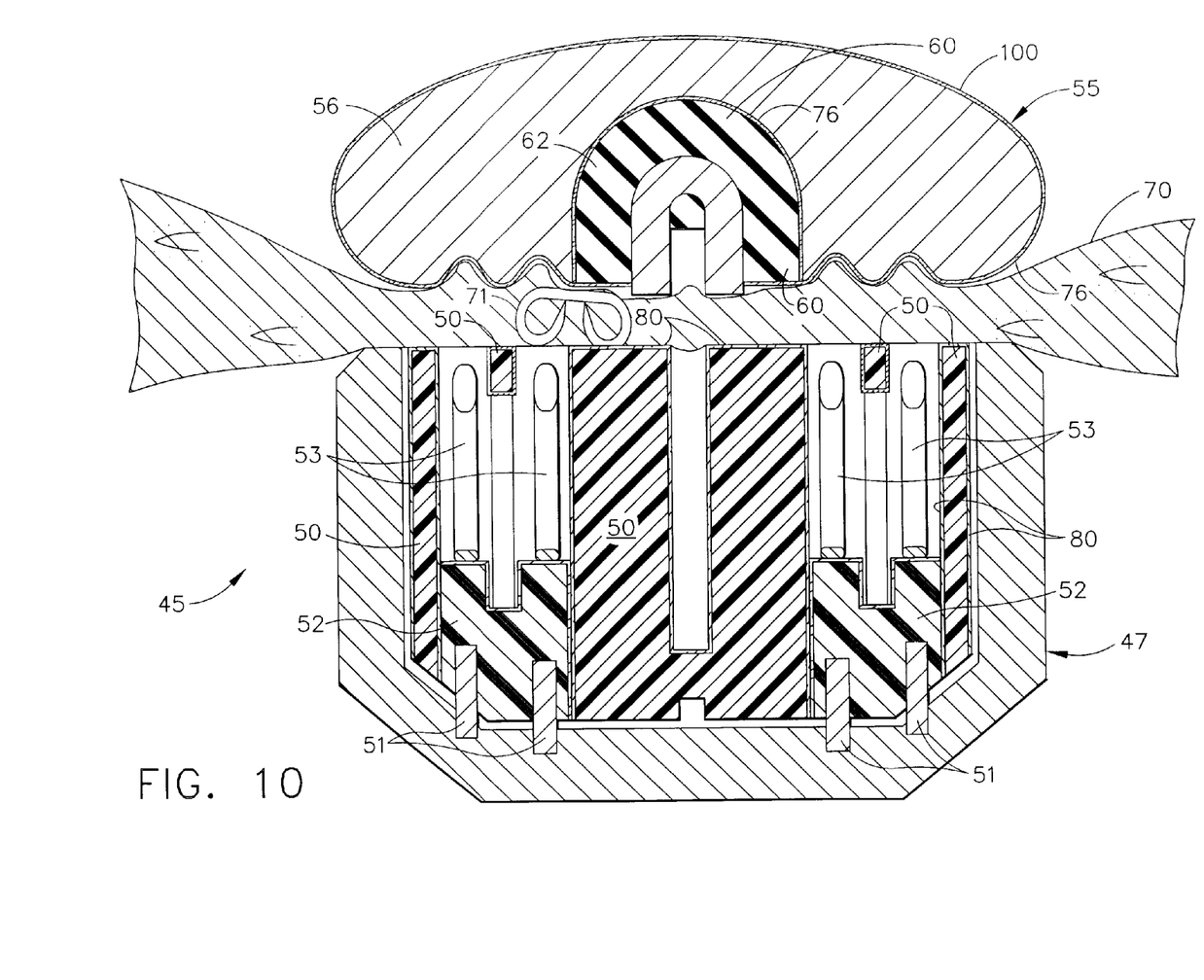
FIG. 10 shows a second alternate anvil coating of the present invention placed on the anvil wherein the anvil coating has no openings along the tissue contact areas.

FIG. 10 shows anvil 55 with an alternate capacitive coupling coating 100 or dielectric coating that can be placed across the entire surface of the anvil 55 with the exception of the electrical contact area at ramp 57 (see FIG. 2). As a consequence, the contact network from the first pole electrode 60, through the tissue 70 and to a second pole electrode 85 (anvil 55 for this example) is blocked by the capacitive coupling anvil coating 100 on the anvil 55 and the tissue coagulation method shifts to capacitive coupling. Whereas the second pole electrode 56 is shown fully coated, a partial coating may suffice provided it creates capacitive coupling circuit with tissue. A rule of capacitance is that the impedance presented by the capacitor is inversely proportional to the frequency. In other words, capacitive coupling favors transfer of the higher frequency components of a signal, and has been found to work well at RF electrosurgical generator frequencies from about 300 kHz to about 3 MHz, and between about 500 kHz and about 700 kHz. Capacitive coupling works well over short distances such as that found between the electrodes of an electrosurgical device. Capacitive coupling coating 100 can be a dielectric such as but not limited to PTFE (polytetrafluroethylene), a Parlene™ or Parylene™, titanium dioxide or an epoxy.

In FIG. 10, tissue 70 contains a formed staple 71 in direct contact with first pole electrode 56 but contact with second pole electrode 56 is prevented by capacitive coupling coating 100. The anvil 55 and second pole electrode 56 can have a large generally flat portion which is prevented from creating a direct contact circuit with the tissue 70 by capacitive coupling coating 100. The surface area of the second pole electrode 56 is much larger than the surface area of the first pole electrode 60. Capacitive coupling circuits with at least one large surface area electrode (second pole electrode 56) and one small surface area electrode (first pole electrode 60) can exhibit a subtle but different effect. This effect works as follows. There is a threshold of electrosurgical energy density in tissue that must be met before tissue effects can occur. When the energy density is below the threshold, the tissue is unaffected by the application of energy. When the energy density rises above the threshold, the tissue is affected by the energy and begins to heat or cook. With the second alternate anvil coating 100 of the present invention, the energy density is spread between the first and second pole electrodes 60, 56, somewhat analogous to magnetic lines of force between two magnets. This concentrates the energy density at the first pole electrode 60 and spreads or dilutes the field lines across the horizontal surface of second pole electrode 56. When a small metallic object, such as formed staple 71 is present in tissue 70 of the above capacitive circuit, the capacitive coupled RF energy can ignore the small area of the conductive staple 71 as a path of least resistance. This means capacitive coupling coagulation can occur near the first pole electrode and not around the formed staple 71, unlike contact RF circuits.

Figure 11:
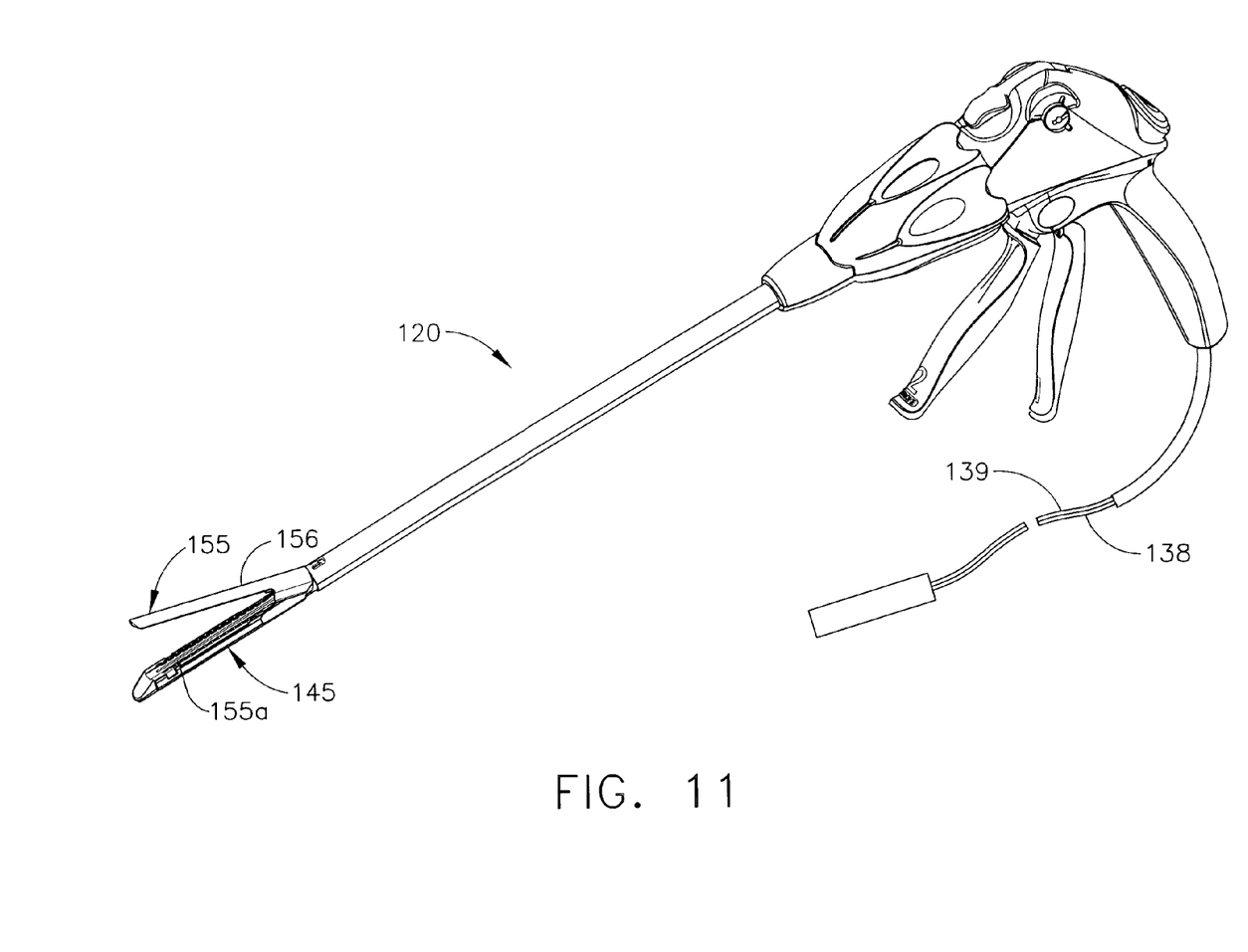
FIG. 11 shows an alternate E-beam electrosurgical instrument 120 of the present invention.

FIG. 11 shows an alternate E-beam electrosurgical instrument 120. The E-beam electrosurgical instrument 120 is similar in operation to that of the previously described electrosurgical instrument 20. That is, both electrosurgical instruments clamp, apply RF energy, form rows of staples in the tissue, and cut the tissue between the innermost rows of staples. E-beam electrosurgical instrument 120 has first and second pole E-beam wires 138, 139 respectively. These e-beam wires 138, 139 are attachable to generator 21 and foot switch 22 (See FIG. 1) by connector 140 to deliver RF energy to an E-beam end effector 145. The E-beam end effector 145 of the alternate electrosurgical instrument 120 has some mechanical improvements over the original electrosurgical instrument 20.

Figure 12:
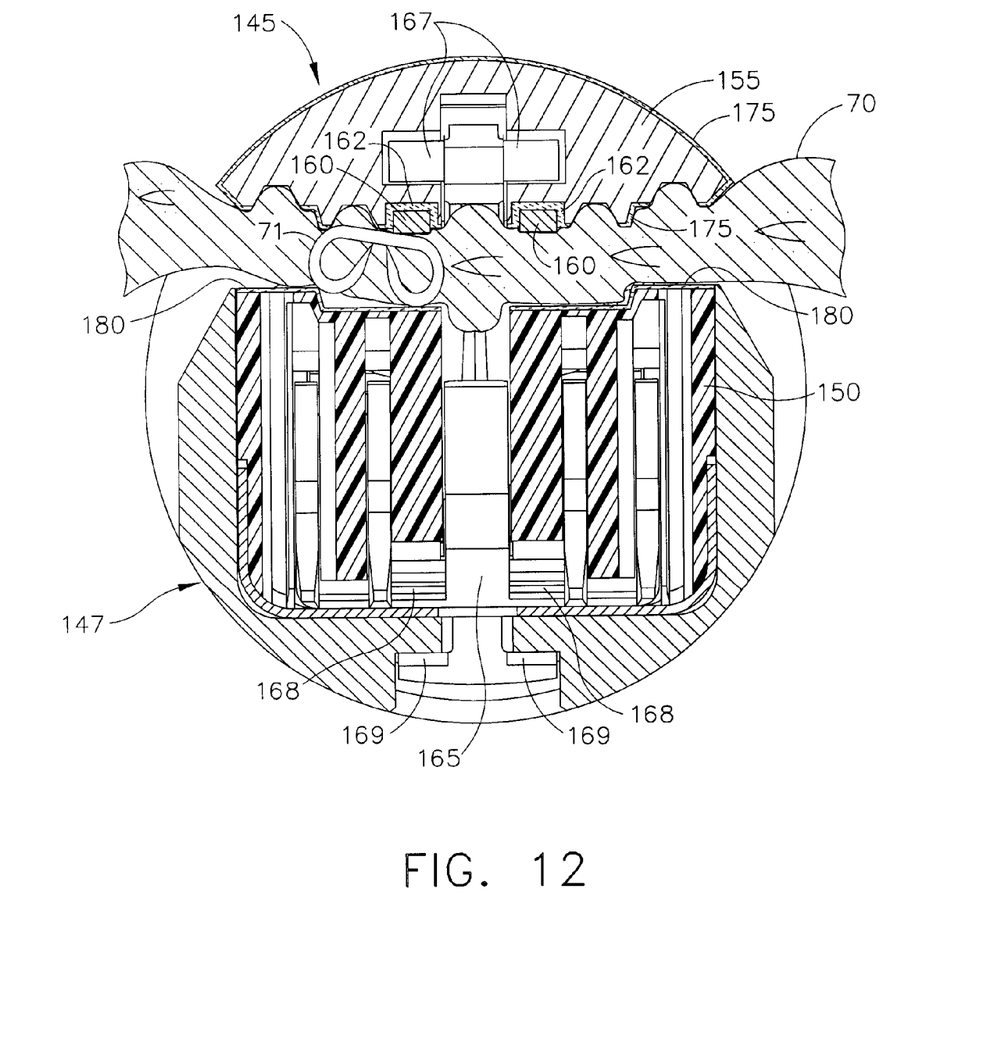
FIG. 12 is a cross sectional view of the E-beam end effector of FIG. 11 clamped on tissue containing one formed staple and showing how an anvil coating prevents shorting between a first pole electrode and anvil.

As best shown in FIG. 12, the alternate electrosurgical instrument has an E-beam 165 that travels through the end effector 145 during firing to maintain a uniform tissue gap between an E-beam anvil 155 and an E-beam channel 147. E-beam 165 has upper supports 167 that travel within an anvil slot (in anvil 155 about upper supports 167), lower supports 169 that travel below a channel slot 148 and middle supports 168 that run along an inner surface of E-beam channel 147.

E-beam upper supports 167 and E-beam lower supports 169 tie the E-beam anvil 155 and an E-beam channel 147 together in the vertical direction prevent spreading of the end effector 145 from thick tissue. E-beam upper supports 167 and E-beam middle supports 168 prevent the E-beam end effector 145 from coming together when clamped on thin tissue. Since E-beam cartridge 150 mounts within E-beam channel 147, the tissue gap between E-beam cartridge 150 and E-beam anvil 155 is also maintained. E-beam electrosurgical instruments such as E-beam electrosurgical instrument 120 are well known in the art such as that found in US. Patent Publication number 20040232196 by Shelton et al. and filed on May 20, 2003 which is incorporated herein in its entirety by reference.

The E-beam mechanism has necessitated some changes in the design of the first pole electrode 60, insulator 62 and second pole electrode 56 of the electrosurgical instrument 20. As shown in FIG. 11, the electrode design of beam electrosurgical instrument 120 has a pair of E-beam first pole electrodes 160 mounted on E-beam insulators 162. E-beam anvil 155 acts as E-beam second pole electrode 156. Tissue 70 is shown clamped within The E-beam end effector 145 and a formed staple 71 is in contact with one of the E-beam first pole electrodes 160 and in contact with E-beam anvil coating 175. E-beam anvil coating 175 prevents contact of the formed staple 71 with E-beam second pole electrode 156. E-beam cartridge coating 180 prevents the formation of a surface charge on the E-beam cartridge 150.

Whereas the above stapling devices are straight, it would be obvious to one skilled in the art to apply the coatings to anvils and cartridges of any stapling device of any shape, including but not limited to actuator circular. Alternately, staples or other conductive fasteners used in the body could also be coated in dielectric coatings, the dielectric coatings making the staples nonconductive when subjected to electrosurgical energy. Dielectric staple coatings could be but are not limited to PTFE (polytetrafluroethylene), a Parlene™ or Parylene™, titanium dioxide or an epoxy.

It will be recognized that equivalent structures may be substituted for the structures illustrated and described herein and that the described embodiment of the invention is not the only structure which may be employed to implement the claimed invention. As one example of an equivalent structure which may be used to implement the present invention, a coating such as PTFE can be used as a dielectric coating in a bipolar electrosurgical device. As a further example of an equivalent structure which may be used to implement the present invention, an alternate coating such as a coating having polymers based on paraxylene can be used as a dielectric coating in a bipolar electrosurgical device.

While preferred embodiments of the present invention have been shown and described herein, it will be obvious to those skilled in the art that such embodiments are provided by way of example only. Numerous variations, changes, and substitutions will now occur to those skilled in the art without departing from the invention. Accordingly, it is intended that the invention be limited only by the spirit and scope of the appended claims.

What is claimed is:

1. An electrosurgical instrument having an end effector capable of clamping on tissue and receiving RF bipolar energy therein, said end effector comprising:
    a) a first pole electrode having a first tissue contact surface;
    b) a second pole electrode having a second tissue contact surface with at least one pocket recessed therein; and
    c) a dielectric coating placed on said second pole electrode across said second tissue contact surface and into said at least one pocket, said dielectric coating having at least one open channel recessed deep into said at least one open pocket and extending through said dielectric coating to provide passage of radio frequency energy between said first and second pole electrodes, wherein when the end effector is clamped without tissue therein, said first and said second pole electrodes are configured to prevent shorting contact therebetween, wherein when the end effector is clamped with at least one electrically conducting object therein, said first and second pole electrodes and said dielectric coating are configured to prevent said at least one electrically conducting object from directly shorting said first and second pole electrodes together.

2. The electrosurgical instrument of claim 1 wherein at least one of said first pole electrode or said second pole electrode includes at least one staple forming pocket therein in direct opposition to a staple positioned for ejection from within the end effector, said staple forming pocket configured to secure said staple into tissue as said staple is ejected, wherein at least a portion of said at least one staple forming pocket is free of dielectric coating and provides at least one open channel through said dielectric coating.

3. The electrosurgical instrument of claim 2 wherein said electrosurgical instrument includes at least one electrically conductive staple formable against one of said first pole electrode or said second pole electrode.

4. The electrosurgical instrument of claim 3 wherein said electrically conductive staple has a dielectric coating.

5. The electrosurgical instrument of claim 1 wherein said dielectric coating contains at least one coating selected from the group of polytetrafluroethelene, at least one of a series of polymers based on paraxylene, titanium dioxide, and epoxy.

6. The electrosurgical instrument of claim 5 wherein said at least one channel is in said dielectric coating, on at least one of said first pole electrode or said second pole electrode, and comprises one or more of an open channel:
    a) etched through said dielectric coating with sandblasting,
    b) etched through said dielectric coating with water jetting,
    c) ground in place through said dielectric coating, or
    d) etched through said dielectric coating with laser etching.

7. The electrosurgical instrument of claim 5 wherein said dielectric passage is selectively masked from areas of said first pole electrode or said second pole electrode to prevent dielectric coatings from adhering thereto, said selectively masked areas having a masked edge around each dielectric passage.

8. The electrosurgical instrument of claim 1 wherein said dielectric coating comprises one or more of:
    a) a generally constant thickness, or
    b) a variable thickness.

9. The electrosurgical instrument of claim 1 further including a knife moveable through the end effector.

10. The electrosurgical instrument of claim 1, wherein the end effector further comprises a first clamping member and a second clamping member, wherein the second clamping member is movable toward the first clamping member, wherein the second clamping member includes both the first pole electrode and the second pole electrode.

11. An electrosurgical instrument having an end effector for clamping and coagulating tissue with bipolar energy, said end effector comprising:
    a) a first clamping member;
    b) a second clamping member, wherein the second clamping member is movable toward the first clamping member to clamp tissue between the first clamping member and the second clamping member, wherein the second clamping member comprises:

i) a first pole electrode having a first contact surface configured to provide a contact for tissue, and ii) a second pole electrode having a second contact surface configured to provide a contact for tissue, said second pole electrode having at least one pocket recessed therein; and c) a dielectric coating entirely covering the second pole electrode of the second clamping member, said dielectric coating having at least one open channel recessed into said at least one pocket and extending through said dielectric coating to provide passage of radio frequency energy between said first and second pole electrodes, said dielectric coating placing a non-conducting barrier between said first pole electrode of the second clamping member and said second pole electrode of the second clamping member.

12. The electrosurgical instrument of claim 11 wherein said dielectric coating creates a capacitive coupling circuit when clamping and coagulating tissue between the first and second clamping members, the capacitive coupling circuit being created with the first and second pole electrodes of the second clamping member.

13. The electrosurgical instrument of claim 11 wherein said bipolar energy is radio frequency energy.

14. The electrosurgical instrument of claim 11 wherein said dielectric coating is at least one selected from the group of polytetrafluroethelene, at least one of a series of polymers based on paraxylene, titanium dioxide, and epoxy.

15. The electrosurgical instrument of claim 11 further including a knife moveable through the first clamping member.

16. The electrosurgical instrument of claim 11, wherein the first pole electrode extends along a central portion of the second clamping member, wherein at least part of the second pole electrode is positioned lateral to the first pole electrode.

17. The electrosurgical instrument of claim 11, wherein the second clamping member further comprises an insulator separating the first pole electrode from the second pole electrode, wherein the insulator has a C-shaped cross-section, wherein the dielectric coating is further positioned between the second pole electrode and the insulator.

18. The electrosurgical instrument of claim 11, wherein the second clamping member further comprises a plurality of staple forming pockets.

19. The electrosurgical instrument of claim 18, wherein the plurality of staple forming pockets are formed in the second pole electrode, wherein the dielectric coating extends fully into the staple forming pockets.

20. An electrosurgical instrument having an end effector capable of applying bipolar energy and placing at least one staple into tissue compressed therein, said end effector comprising;

a) a first pole electrode having a first tissue contact surface;

b) a second pole electrode, wherein the second pole electrode has a second tissue contact surface defining a recess, wherein the recess is positioned opposite one of the at least one staple positioned for ejection from within the end effector, wherein the recess is configured to secure the one of at least one staple into tissue as the staple is ejected; and c) a dielectric coating on the second pole electrode, wherein the dielectric coating extends across at least a portion of the second tissue contact surface, wherein the dielectric coating further defines an opening at the recess providing a passageway through the recess for radio frequency energy to be communicated between the first pole electrode and the second pole electrode, wherein the end effector is configured to clamp tissue such that the first and second pole electrodes and the dielectric coating are configured to prevent the tissue from directly shorting the first and second pole electrodes.

21. The electrosurgical instrument of claim 20 wherein said coating is a dielectric comprising at least one selected from a group of polytetrafluroethelene, at least one of a series of polymers based on paraxylene, titanium dioxide, and epoxy.

22. The electrosurgical instrument of claim 20 further including a knife moveable through the end effector.

23. The electrosurgical instrument of claim 20, wherein the recess comprises a staple forming pocket.

24. An electrosurgical instrument having an end effector capable of applying bipolar energy and placing at least one fastener into tissue compressed therein, said end effector comprising;

a) a first pole electrode having a first tissue contact surface;

b) a second pole electrode, wherein the second pole electrode has a second tissue contact surface defining a staple forming pocket; and c) a dielectric coating on the second pole electrode, wherein the dielectric coating extends across at least a portion of the second tissue contact surface, wherein the dielectric coating further defines an opening at the staple forming pocket providing a passageway through the staple forming pocket for radio frequency energy to be communicated between the first pole electrode and the second pole electrode.

25. The electrosurgical instrument of claim 24, wherein said dielectric coating on said staple is at least one selected from the group of polytetrafluroethelene, at least one of a series of polymers based on paraxylene, titanium dioxide, and epoxy.

* * * * *